United States Patent

Golec, Jr. et al.

[11] 4,331,600
[45] May 25, 1982

[54] INTERMEDIATES FOR THE SYNTHESIS OF PHTHALIMIDINES

[75] Inventors: Frederick A. Golec, Jr., Ossining; Joseph Auerbach, Brooklyn, both of N.Y.

[73] Assignee: USV Pharmaceutical Corporation, Tuckahoe, N.Y.

[21] Appl. No.: 202,812

[22] Filed: Oct. 31, 1980

[51] Int. Cl.$^3$ .................. C07D 209/46; C07D 265/02; C07D 307/88
[52] U.S. Cl. ................................. 548/472; 424/248.5; 424/274; 544/63; 562/429; 562/430; 549/307
[58] Field of Search ................................. 260/325 PH

[56] References Cited

U.S. PATENT DOCUMENTS 4,188,330 2/1980 Giacobbe et al. ............ 260/325 PH

FOREIGN PATENT DOCUMENTS 1025904 4/1966 United Kingdom ......... 260/325 PH

*Primary Examiner*—Alton D. Rollins

[57] ABSTRACT

Compounds of the formula

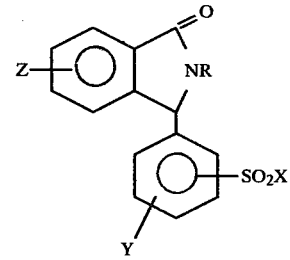

wherein,

Y and Z are each H, alkyl, halo, alkoxy, trifluoromethyl, hydroxy, alkanoyloxy, or alkanoylamino;

X is F, Cl Br or $NR_1R_2$ in which $R_1$ and $R_2$ are each hydrogen, alkyl, alkenyl, alkynyl, aryl, aralkyl or cycloalkyl; and R is H, alkyl, cycloalkyl or aralkyl; and salts thereof.

The compounds have utility as anti-hypertensive and diuretic agents and as intermediates for the preparation of other anti-hypertensive and diuretic agents.

6 Claims, No Drawings

INTERMEDIATES FOR THE SYNTHESIS OF PHTHALIMIDINES

This invention relates to new intermediates for the preparation of certain phthalimidines and phthalazinones. The intermediates are more particularly concerned with the preparation of 3-aryl-3-hydroxyphthalimidines which are useful as therapeutic agents.

The 3-aryl-3-hydroxyphthalimidines produced in accordance with the present invention are compounds of the formula:

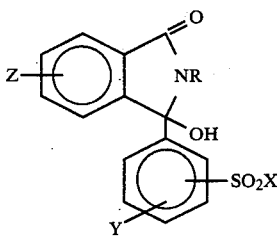

wherein,
Y and Z are each H, alkyl, halo, alkoxy, trifluoromethyl, hydroxy, alkanoyloxy, or alkanoylamino;
X is F, Cl, Br or $NR_1R_2$ in which $R_1$ and $R_2$ are each hydrogen, alkyl, alkynyl, alkenyl, cycloalkyl, aryl or aralkyl; and
R is H, alkyl, cycloalkyl, or aralkyl.

Some of the said compounds are known and are characterized by valuable therapeutic activity. For example, chlorthalidone, 3-hydroxy-3-(3'-sulfamyl-4-chlorophenyl)phthalimidine, is widely used as an anti-hypertensive and diuretic, and for treatment of renal or cardiovascular disorders. A substantial number of the said compounds are also useful as therapeutic agents for the same purposes.

The compounds of formula I are prepared in accordance with the present process by oxidation of the corresponding desoxy compounds represented by the formula:

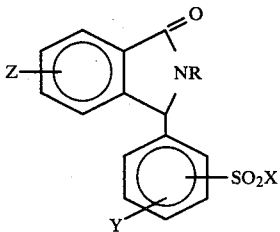

wherein X, Y, Z and R are each as previously described.

The total number of carbon atoms in each hydrocarbyl substituent described in Formulae I and II can range up to about 10, and these substituents can be branched or straight-chained. The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of Formula I are those prepared from compounds of the formula:

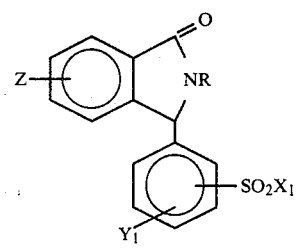

wherein,
R and Z are as hereinbefore described;
$Y_1$ is halo or $CF_3$; and
$X_1$ is Cl, Br or $NR_1R_2$ wherein each of $R_1$ and $R_2$ is hydrogen, alkyl, alkynyl, alkenyl, cycloalkyl, aryl or aralkyl.

The desoxy compounds of Formula II, and Formula III, are converted to corresponding compounds of Formula I by oxygenation at the 3-position of the phthalimide ring. Such oxidation can be accomplished by the usual methods employed in benzylic oxidation, e.g., *Helv. Chem. Acta*, 42, 1085 (1959) and *Chem. Ber.*, 103, 3783 (1970) wherein oxidation of 3-(4'-chlorophenyl)phthalimidine to the corresponding 3-hydroxy compound is described employing chromic acid-acetic acid as the oxidizing agent.

The oxidation can also be accomplished by simple contact with oxygen or an oxygen-containing gas with or without catalyst present. The catalysts include ferrous ammonium sulfate, cupric sulfate, cobalt naphthenate, cuprous chloride and zinc chloride, all of which gave varying yields, in part predicated on varying time of reaction. Usually, reaction times can range from as little as about 8 hours up to about 24 hours and even longer. Significant yields of product are obtained when the reaction time ranges from about 15 to about 20 hours which is preferred when a catalyst is employed. Without added catalyst, the reaction times are considerably longer ranging from about 48 hours up to 72 hours for significant yields to be obtained. When oxygen is employed as the oxidant, the reaction is conveniently effected at room temperature as a matter of convenience, since temperature does not play a critical role in the reaction.

As an alternative to the foregoing oxidative methods, there may be employed the usual oxidizing agents alone or in combination to accomplish the desired oxygenation. For example, oxidants such as permanganates, peroxides, chromates, hypochlorites, such as t-butyl and sodium hypochlorite, manganese dioxide, periodates, ferric ammonium sulfate, bromine and the like can be used. The time of reaction is usually within the range of 0.5 hour to about 60 hours depending on the reagent selected and the yield of product sought. For example with manganese dioxide, as little as one hour is sufficient to obtain high yields of the oxygenated product, whereas reaction times of up to 100 hours may be required with reagents such as ferric ammonium sulfate-cupric sulfate in water at room temperature.

In most cases, aqueous reaction media are employed and can be comprised of water alone or in mixtures with water-miscible polar solvents such as dimethylformamide, tetrahydrofuran, acetone, dioxane, and the like. In addition, glacial acetic acid can be used as solvent, or in mixtures with water as co-solvent. Conveniently, the deoxy phthalimidine can react with alkali to form water-soluble salts and, for more efficient oxidation, the substrate compounds are usually dissolved in water, or the aqueous solvent, by use of suitable alkali, such as sodium hydroxide, potassium hydroxide, sodium carbonate and potassium carbonate. The oxygenated products can be recovered from the aqueous reaction medium by merely acidifying and thereafter extracting the mixture with suitable organic solvents from which the product can be separated using known techniques.

In the desoxy compounds, used as starting materials for the oxygenation, it is preferred to avoid the presence of substituents (X, Y and Z) which would be reactive with oxidants under the reaction conditions. Thus, reactive groups such as amino groups, where present, should be blocked as by acylation and the blocking group removed after oxidation is completed. Alternatively, the reactive group, such as amino, can be formed after oxygenation, e.g. by reducing nitro to amino, and as necessary, converting amino to other substituents.

The desoxy compounds of Formula II can be prepared by conversion of the corresponding benzoxazinones of the formula:

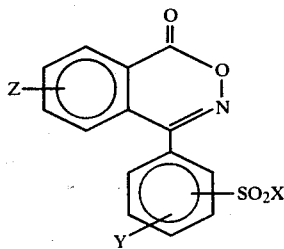

IV wherein X, Y and Z are as hereinbefore defined.

The preferred compounds are those of formula IV wherein Y is halo or $CF_3$ and X is $NR_1R_2$ as previously described.

The conversion of formula IV compounds to those of formula III is accomplished by deoxygenation, i.e., removal of the hetero oxygen atom from the oxazinone ring. This reduction can be accomplished by art-recognized procedures such as using zinc metal, conveniently zinc dust and acid. The starting compound is dissolved in a suitable solvent system, usually a polar solvent, preferably water-miscible, as previously described. The water-miscible solvent is convenient since it permits ready precipitation of the product by dilution with water. The solvent, starting compound, acid and zinc dust are heated conveniently at the reflux temperature of the solvent system for reaction periods of about one to about four hours. For efficient reaction, the zinc dust is used in excess, usually about 10-20 fold molar excess, and the dust is added portionwise to the refluxing reaction mixture. After completion, the reaction mixture is diluted with cold water after removal of the zinc dust and the product separates.

Compounds of Formula II can be prepared by substitution of compounds of the following formula:

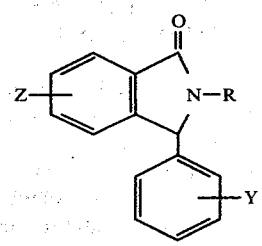

V wherein Y, Z and R are each as previously described to introduce substituent $SO_2X$, e.g. by halosulfonation to form the sulfonyl halide followed by reaction with basic nitrogen compounds to form the sulfamyl group, e.g. reaction with ammonia to form the sulfonamide group.

Further, compounds of Formula II can be obtained by reduction of compounds of the formula:

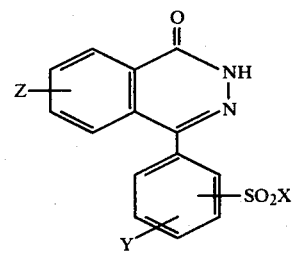

VI wherein X, Y and Z are as hereinbefore described, using reduction processes known for this reaction, such as zinc metal reduction. The starting compound dissolved in organic solvent, preferably water-miscible as herein previously described, and the zinc metal is added along with a mineral acid such as sulfuric or hydrochloric acids. The reaction is usually carried out at elevated temperature although room temperature will suffice. Conveniently, the reflux temperature of the reaction mixture can be used as reaction temperature. The reaction proceeds quite rapidly and is usually complete in relatively short periods of time. Heating for about 1-2 hours is desirable to assure maximum yields, particularly at temperatures between 50° and 100° C.

The product is obtained by pouring the reaction mixture into water and thereafter filtering or extracting with suitable organic solvent, e.g. ethylacetate, to remove the product. The organic solvent can then be removed to obtain the product as residue.

The compounds of formula II herein can also be prepared from the corresponding phthalides of the following formula:

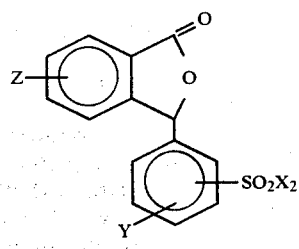

VII wherein,
Z and Y are as previously described; and
$X_2$ is fluoro, chloro or bromo.

The preferred compounds are those in which Y is halo or trifluoromethyl. A useful class of the phthalide intermediates are those in which Y is in the 4-position and SO₂X is in the 3-position of the phenyl group to which they are attached.

The aforesaid phthalide compounds can be converted to the corresponding phthalimidines by treatment with ammonia or an ammonium derivative by known procedures, e.g. as described in U.S. Pat. No. 3,055,904.

Intermediate compounds of the Formulae V and VI are known and can be prepared by art-recognized procedures. For example, compounds of Formula V can be prepared from the corresponding phthalazinones or the corresponding benzoxazinones, usually by treatment with zinc dust by the method hereinbefore described. The phthalazinone compounds of Formula VI can be prepared by substitution reactions of the corresponding compounds wherein substituent Y is H, by substitution methods hereinbefore described.

Employing the procedures described herein, a variety of compounds of formulae II, III, IV, V and VI can be prepared with various substituent as hereinafter illustrated:

| R | Z | X | Y |
|---|---|---|---|
| CH₃ | H | NH₂ | CF₃ |
| CH₃ | H | NH₂ | CF₃ |
| CH₃ | H | Cl | CF₃ |
| C₂H₅ | H | Cl | Cl |
| CH₃ | H | NH₂ | CF₃ |
| CH₃ | H | NHCH₃ | OC₄H₉ |
| CH₃ | H | NH₂ | Cl |
| C₃H₇ | H | NHC₆H₅ | CF₃ |
| C₄H₉ | H | N(CH₃)₂ | CF₃ |
| C₆H₁₃ | H | NHCH₂C₆H₅ | Cl |
| i-C₄H₉ | OCH₃ | NH₂ | CF₃ |
| H | H | NH₂ | OCH₃ |
| C₆H₅CH₂ | NO₂ | CH₃ | CH₃ |
| C₆H₁₁ | H | Cl | CH₂C₆H₅ |
| H | H | NH₂ | C(CH₃)₃ |
| C₆H₅ | OC₃H₇ | NH₂ | C₆H₅ |
| H | H | Cl | Cl |
| H | Cl | Cl | Cl |
| H | Cl | Br | Cl |
| H | OCH₃ | NH₂ | C₅H₁₁ |
| H | H | NH₂ | H |
| H | H | NH₂ | H |
| H | H | NH₂ | OH |
| H | H | Br | Cl |
| H | CH₃O | Br | Br |
| H | H | Cl | CH₃ |
| H | H | Cl | Cl |
| H | H | NH₂ | Cl |
| H | OC₃H₇ | Cl | Cl |
| H | H | NH₂ | Cl |
| H | H | NHC₆H₁₁ | OH |
| H | CH₃COO | N(CH₃)₂ | OOCCH₃ |
| H | H | NHC₄H₉ | H |
| H | H | NH₂ | Cl |
| H | H | Cl | CF₃ |
| H | H | NH₂ | H |
| H | OCH₃ | Cl | H |
| H | H | NH₂ | OCH₃ |
| H | H | Cl | OCH₃ |
| H | OCH₃ | Cl | CF₃ |
| H | H | NH₂ | CF₃ |
| H | OCH₃ | NH₂ | CF₃ |
| H | H | NH₂ | Cl |
| H | H | NH₂ | Br |
| H | H | NH₂ | NHCOCH₃ |

Formula IV compounds include the following:

| R | Z | X | Y | Z' |
|---|---|---|---|---|
| CH₃ | H | NH₂ | CF₃ | O |
| CH₃ | H | NH₂ | CF₃ | O |
| CH₃ | H | Cl | CF₃ | NH |
| C₂H₅ | H | Cl | Cl | NCH₃ |
| CH₃ | H | NH₂ | CF₃ | NC₆H₁₁ |
| CH₃ | H | NHCH₃ | OC₄H₉ | N CH₂C₄H₅ |
| CH₃ | H | NH₂ | Cl | NC₄H₉ |
| C₃H₇ | H | NHC₆H₅ | CF₃ | O |
| C₄H₉ | H | N(CH₃)₂ | CF₃ | O |
| C₆H₁₃ | H | NHCH₂C₆H₅ | Cl | O |
| i-C₄H₉ | OCH₃ | NH₂ | CF₃ | NCH₃ |
| H | H | NH₂ | OCH₃ | NC₆H₁₃ |
| C₆H₅CH₂ | NO₂ | CH₃ | CH₃ | O |
| C₆H₁₁ | H | Cl | CH₂C₆H₅ | O |
| H | H | NH₂ | C(CH₃)₃ | O |

The desoxy compounds of Formulae II and III and the benzoxazinones of Formula IV are new compounds and are useful as intermediates in the present process. The said desoxy compounds also possess therapeutic activity useful in the treatment of renal or cardiovascular disorders, or as anti-allergic agents. In therapeutic usage, the compounds themselves can be employed or, as desired, salts thereof with alkali or alkaline earth metals. The alkali metal, e.g., Na, K and Li, salts in particular are especially useful in view of their water solubility especially in the formation of aqueous therapeutic compositions. The alkaline earth metal, e.g., Ca, Mg, Ba, Sr, are especially useful in the purification and/or isolation of the desoxy compounds in view of their more limited water solubility. The Ca and Mg salts are also useful in therapeutic formulations where only limited water solubility of the active ingredient is desired.

Of course, where basic substituents are present in the desoxy compounds, such compounds can form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new basic compounds are contemplated by the present invention.

The pharmaceutically-acceptable acid addition salts are of particular value in therapy. These include salts of mineral acids such as hydrochloric, phosphoric, metaphosphoric, nitric, sulfuric acids, as well as salts of organic acids such as tartaric, acetic, citric e.g., p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new deoxy compounds of Formulae II and III are useful as anti-hypertensive agents and diuretic agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumtances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Preparation of 3-(3'-sulfamyl-4'-chlorophenyl)phthalimidine from 3-(4'-chlorophenyl)phthalimidine To a stirred suspension of 3-(4'-chlorophenyl)phthalimidine (5.00 g., 20.5 mmol) in dry (via 3A molecular sieves) chloroform (25 ml.) is added dropwise chlorosulfonic acid (6.0 equiv., 8.0 ml., 120 mmol) and the solution is heated under reflux for 3 hours. Additional chlorosulfonic acid (6.0 equiv., 8.0 ml., 120 mmol) is added and reflux continued for 0.5 hours. The solution is then added dropwise to crushed ice (400 ml.) Ammonia gas is bubbled into the suspension until pH=10.0 and reaction as evidenced by solution occurs. The entire reaction mixture is concentrated in vacuo to remove the chloroform and the resulting aqueous solution is adjusted to pH $\approx$ 7.0 with glacial acetic acid to yield a precipitate. The precipitate is collected by vacuum filtration and dried under vacuum to yield the crude product: 4.68 g. This crude product is recrystallized from aqueous dimethyl formamide to yield a first crop of product having a melting point of 249°–250° C. and weighing 2.61 g. Anal. calculated for $C_{14}H_{11}N_2O_3SCl$: C, 52.26; H, 3.13; N, 8.71. Found: C, 52.24; H, 3.38; N, 8.45.

EXAMPLE 2

Preparation of 3-hydroxy-3-(3'-sulfamyl-4'-chlorophenyl)phthalimidine from 3-(3'-sulfamyl-4'-chlorophenyl)phthalimidine

Method A

To a stirred solution of 3-(3'-sulfamyl-4'-chlorophenyl)phthalimidine (1.00 g., 3.09 mmol) in glacial acetic acid (25 ml.) is added 8.0 ml. of a 1 M solution of chromic acid in aqueous acetic acid (16.56 mmol of chromic acid), made by dissolving 21.0 g. (0.21 mol) of chromic anhydride in 190 ml. of glacial acetic acid followed by the addition of 10.0 ml. (0.56 mol) of water, via an addition funnel over a four hour period. After one hour additional reaction time the product is isolated by dilution of the reaction mixture with water and extraction into ethyl acetate. The ethyl acetate layer is dried over calcium chloride, filtered and the filtrate concentrated in vacuo to yield 900 mg. of the crude product. Recrystallization from ethyl acetate/toluene gave the product having a melting point of 230°–240° C. and weighing 600 mg.

Method B 3-(3'-sulfamyl-4'-chlorophenyl)phthalimidine is suspended in distilled water (500 mg., 1.55 mmol in 20 ml.) and with stirring 50% aqueous sodium hydroxide is added dropwise until solution is complete (requires 1 ml.) Air is passed through a pre-saturation chamber of water and then directly into the reaction mixture for a period of 65 hours. The solution is acidified to pH=3.0 with concentrated hydrochloric acid, diluted with water (100 ml.) and the product isolated by partitioning with ethyl acetate (100 ml.). The ethyl acetate extract is dried over sodium sulfate, filtered to remove the drying agent and the filtrate concentrated in vacuo to yield 590 mg. of crude product. The crude product is dissolved in ethyl acetate, diluted with an equal volume of toluene and the solution concentrated in vacuo at room temperature to remove the ethyl acetate. The resulting toluene insoluble precipitate is collected by vacuum filtration to yield 230 mg. of product having a melting point greater than 240° C.

Method C

In a 25 ml round bottom reaction vessel is placed 50 mg. deoxycompound (0.155 mmol); then 4 ml. of 1 normal sodium hydroxide solution is added; the reactants are soluble at room temperature. Then 1 ml. of 30% hydrogen peroxide solution is added. After 24 hours the reaction is worked up by adding 15 ml. of 2 molar citric acid and transferred to a separatory funnel where the reaction mixture is extracted with ethyl acetate. The ethyl acetate is cross washed with water, sodium bicarbonate solution, and brine. The ethyl acetate is separated, dried with magnesium sulfate, clarified and evaporated. An infrared spectrum of the product along with an NMR spectrum and TLC indicated the formation of 3-hydroxy-3-(3'-sulfamyl-4'-chlorophenyl)-phthalimidine.

Method D

In a 25 ml round bottom reaction vessel is placed deoxycompound 50 mg (0.155 mmol) and 2 ml of 1 normal sodium hydroxide solution. The reactants are soluble in this medium. At room temperature add 4 ml of 0.1 normal potassium permanganate solution. As permanganate is added the blue color of the reagent discharges and a brown precipitate forms. The last ml of reagent resulted in a permanent purple tint to the reaction mixture. Thin layer chromatography of the reaction mixture at this time revealed rapid conversion of the deoxycompound to 3-hydroxy-3-(3'-sulfamyl-4'-chlorophenyl)-phthalimidine. The reaction mixture was allowed to stir overnight. Workup consisted of acidification of the reaction mixture with 2 N HCl and addition of aqueous sodium bisulfite 10 ml. The reaction mixture was extracted with ethyl acetate, cross washed with water and sodium bicarbonate solution and finally brine. The ethyl acetate was separated, dried with magnesium sulfate, clarified and evaporated to dryness, to obtain the product.

Additional Methods

These processes were carried out in a manner as described in Method B except for variations in solvents and temperatures and the presence of inorganic catalysts as noted in Table I.

TABLE 1

| Method | Catalyst (equiv.) | Solvent | Temp. | Reaction Time[1] | % Yield[2] |
|---|---|---|---|---|---|
| E | $MnO_2$ (3.6) | 40% aq. DMF | reflux | 1.5 | 72 |
| F | Pd on Carbon (.03) | 40% aq. DMF | reflux | 24 | * |
| G | $Br_2$ (2.0) | 5% aq. NaOH | r.t. | 54 | 102 |
| H | $Br_2$ (2.0) | 5% aq. NaOH | r.t. | 16 | 79 |
| I | Co(naphthenate) (0.63) | 10% aq. NaOH | r.t. | 16 | 24 |
| J | $Fe(NH_4)_2(SO_4)_2$ (0.65) | 5% aq. NaOH | r.t. | 16 | 40 |
| K | $CuCl_2$ (1.0) | 2.5% aq. NaOH | r.t. | 18 | 67 |
| L | $CuSO_4$ (1.0) | 2.5% aq. NaOH | r.t. | 18 | 97 |
| M | $ZnCl_2$ (1.0) | 2.5% aq. NaOH | r.t. | 18 | 78 |

*not determined
[1] in hours
[2] stoichiometric

In all cases of Methods E-M, the appropriate 3-hydroxy-3-aryl-phthalimidine was identified by TLC techniques against known standards. The TLC technique used was one based on a solvent system composed of 1,2-dichloroethane/ethanol/ammonium hydroxide (28%) (80/20/5).

EXAMPLE 3

Preparation of
4-(3'-sulfamyl-4'-chlorophenyl)phthalazin-1-one from
4-(4'-chlorophenyl)phthalazin-1-one 4-(4'-Chlorophenyl)phthalazin-1-one (3.99 g., 15.54 mmol) is added to chlorosulfonic acid (10.0 ml., 150.45 mmol, 9.7 equiv.) and the solution stirred for 24 hours at room temperature. The reaction is heated at 120° C. for 18 hours to give complete conversion of starting material to product. The reaction mixture is cooled to room temperature and added dropwise to an ice cold stirred solution of concentrated ammonium hydroxide (100 ml.). The suspension is stirred for 0.5 hour and made strongly alkaline with 50% aqueous sodium hydroxide. Insoluble material (320 mg.) is removed by vacuum filtration, the filtrate adjusted to pH=2.0 with concentrated hydrochloric acid and the precipitate is collected by vacuum filtration. The product weighs 3.40 g. after drying under vacuum (20 mm Hg/60° C.) for 16 hours. The product was identified against a known standard by TLC using two different solvent systems: ethyl acetate/glacial acetic acid (99/1) and methanol/toluene (40/60).

EXAMPLE 4

Preparation of
3-(3'-sulfamyl-4'-chlorophenyl)phthalimidine from
4-(3'-sulfamyl-4'-chlorophenyl)phthalazin-1-one 4-(3'-Sulfamyl-4'-chlorophenyl)phthalazin-1-one (3.36 g., 10.07 mmol) is added to 200 ml. of a solution of dry dimethyl formamide/glacial acetic acid (1:1 v/v) and the resulting suspension heated at 95° to 100° C. Zinc dust (5.00 g., 76.49 mmol) is added portionwise over a twenty minute interval. After 2.5 hours the solution is filtered through celite in order to remove the excess zinc and the filtrate concentrated in vacuo to ca. 50 ml. and diluted with water. The product crystallizes from solution after standing overnight at 5° C. 1.05 grams of product are recovered having the same retention time as a known standard of 4-(3'-sulfamyl-4'-chlorophenyl)phthalimidine (using an ethyl acetate solvent system).

EXAMPLE 5

Preparation of
3-(3'-chlorosulfonyl-4'-chlorophenyl)phthalimidine
from 3-(4'-chlorophenyl)phthalimidine 3-(4'-Chlorophenyl)phthalimidine (2.4 g., 10 mmol) is added to 13.2 ml. of chlorosulfonic acid (200 mmol) and stirred for 0.5 hour at ambient temperature followed by 0.5 hour at 90° C. The product was isolated by pouring the cooled reaction mixture over a mixture of 200 ml. water and 200 g. ice, washing with 400 ml. of methylene chloride, drying the methylene chloride with magnesium sulfate and evaporating off the solvent under vacuum. The residue was taken up in carbon tetrachloride from which crystallized, the product, 3-(3'-chlorosulfonyl-4'-chlorophenyl)phthalimidine.

EXAMPLE 6

Preparation of
4-(3'-chlorosulfonyl-4'-chlorophenyl)phthalazin-1-one
from 4-(4'-chlorophenyl)phthalazin-1-one 4-(4'-chlorophenyl)phthalazin-1-one (2.00 g., 7.79 mmol) was added to chlorosulfonic acid 10.0 ml., 17.53 g., 150.45 mmol) and the solution was heated at 140° C. for 3.5 hours. The solution was then cooled to room temperature and quenched by pouring onto crushed ice (100 g.). The precipitated product was collected by suction filtration and dried under vacuum at 45° C. for 18 hours. The dried product weighed 2.70 g. (98% yield) and melted at 187°-195° C. Mass spectral analysis confirmed the product as 4-(3'-chlorosulfonyl-4'-chlorophenyl)phthalazin-1-one ($M^+$ at 354, $M^+ +2$ at

EXAMPLE 7

Preparation of 3-(3'-sulfamyl-4'-chlorophenyl)-3H-phthalide o-(3'-sulfamyl-4'-chlorobenzoyl) benzoic acid (6.5 g, 19.17 mmol) is added to a solution of methyl amine (20.0 ml, 800 mmol) in acetonitrile (150 ml). After 15 minutes of stirring the resulting solution, methyl amine hydrochloride (3.4 g, 50.3 mmol) and sodium borohydride (1.14 g, 30.11 mmol) are added. The mixture is stirred for 5 hours at room temperature.

The solvent is removed in vacuo and the resulting solid is partitioned between ethyl acetate and dilute aqueous hydrochloric acid. The organic extract is washed with water until neutral, then brine.

The organic extract is concentrated to dryness to yield the crude product, 6.18 g. An analytical sample is obtained by recrystallization from aqueous glacial acetic acid; m.p.=232°–234°. The product is characterized by microanalysis and spectral data.

EXAMPLE 8

Preparation of 3-(4'-chlorophenyl)-3H-phthalide o-(4'-chlorobenzoyl) benzoic acid (25.0 g, 95.9 mmol) is added to a solution of methyl amine (20.0 ml, 800 mmol) in acetonitrile (250 ml). After 15 minutes of stirring the resulting solution, methyl amine hydrochloride (17.0 g, 150 mmol) and sodium borohydride (1.14 gms, 30.11 mmol) are added. The mixture is stirred for 63 hours at room temperature. The solvent is removed in vacuo and the resulting solid is partitioned between ethyl acetate and dilute aqueous hydrochloric acid. The organic extract is washed with 10% aqueous sodium hydroxide, then brine.

The organic extract is concentrated to about ⅓ volume in vacuo, heated to reflux and diluted with hexane to induce crystallization. A 1st crop of crystals weighs 7.1 g. An analytical sample is obtained by recrystallization from aqueous glacial acetic acid, m.p.=124°–125°. The product is characterized by microanalysis and spectral data.

This product is converted to the corresponding 3'-sulfamyl compound by chlorosulfonation and ammonolysis as in the preceding examples.

EXAMPLE 9

The starting compound of Method B of Example 2 is prepared by the following method:

A stirred solution of 4-(3'-sulfamyl-4'chlorophenyl)-5,6-benz-2,3-oxazine-1-one (10.0 g, 29.7 mmol) in a 1:1 mixture (v/v) of dimethyl formamide/glacial acetic acid (250 ml/250/ml) at 85°–90° is treated with zinc dust (15.0 g, 0.23 mol) portionwise over a 25 minute interval. After two hours of heating the solution is vacuum filtered through a celite filter pad to remove excess zinc. The filter pad is not allowed to go to dryness until it is rinsed with a small volume of water. The filtrate is added to 500 ml of ice water, and the precipitate collected by vacuum filtration, and recrystallized from aqueous methanol to yield a first crop; 5.5 g, m.p.=261.5°–262.5°±0.3°.

EXAMPLE 10

The starting compound for Example 9 is prepared by the following method:

o-(3'-Sulfamyl-4'-chlorophenyl)-benzoic acid (25.0 g, 73.7 mmol) and hydroxylamine hydrochloride (20.0 g, 287.6 mmol) are dissolved in a 1:1 solution (v/v) of pyridine (100 ml) and absolute ethanol (100 ml) and the solution is heated for 6 hours. The reaction mixture is poured into ice water (400 ml), the precipitate collected by vacuum filtration and dried under vacuum to give the crude product; 22.33 g, m.p.=275°–280°. Recrystallization of the crude product from aqueous dimethyl formamide gives a first crop of pure product; 10.13 g, m.p.=277°–278°.

EXAMPLE 11

The starting compound for Example 1 is prepared by the following methods:

Method A

To a stirred solution of formic acid (167 ml, 4.43 mol) and formamide (100 ml, 2.50 mol) is added O-(4'-chlorobenzoyl)-benzoic acid (50.00 g, 0.19 mol) and the solution is heated immediately to reflux. The solution is stirred at reflux for 24 hours, during which time crystals precipitate from the solution. The solution is cooled to room temperature and placed into an ice bath for one hour. The product is collected by vacuum filtration and washed with water until neutral to litmus paper. The crude product is dried under vacuum to yield 48.73 g of material. The crude product is recrystallized from a solution of dimethyl formamide/toluene (125 ml/400 ml) to yield a first crop of the product: 21.47 g, m.p.=199.1°–205.4°. A second crop is recovered from the mother liquor; 5.06 g.

Method B 4-(4'-chlorophenyl)-5,6-benz-2,3-oxazine-1-one (57.0 g, 0.22 mol) is dissolved in glacial acetic acid (500 ml) at 100°–105° and zinc dust (31.12 g, 0.48 mol) is added portionwise over a 40 minute interval. The solution is heated and stirred for 1 hour. An additional portion of zinc (5.0 g, 0.076 mol) is added and heating and stirring continued at 110° for 30 minutes. The reaction is completed by addition of excess zinc (11.3 g, 0.17 mmol) with heating continued for 1 hour. The hot solution is filtered through a celite filter pad to remove excess zinc. The filtrate is diluted with water until turbid (250 ml of water is required). The crystallized product is then collected by vacuum filtration to give a first crop; 73.04 g, m.p.=199.7°–203.2°. A second crop of product is recovered from the mother liquor; 9.66 g.

Method C

In a 100 ml reaction vessel is placed 25 ml of isopropanol with good stirring, 2 ml of acetylchloride are added and the mixture allowed to react. After the mild exothermic reaction is over, 3-formamido-1-oxo-3 (p-chlorophenyl) isoindole is added. After refluxing several hours the conversion to product was complete as judged by TLC. The workup of the reaction mixture consisted of filtering off a small amount of insoluble material from the reaction mixture, diluting the filtrate with carbon tetrachoride and concentrating to dryness. The product was further characterized by NMR spectroscopy and a comparison to material prepared by a different method.

EXAMPLE 12

The starting compound of Example 10 is prepared as follows:

o-(4'-chlorobenzoyl) benzoic acid (30.0 g, 11.5 mmol) and hydroxylamine hydrochloride (30.0 g, 43.1 mmol) are dissolved in a solution of pyridine (125 ml) and absolute ethanol (100 ml). The solution is heated under reflux for 5½ hours. The reaction mixture is then poured over 2 liters of crushed ice and the precipitate collected by vacuum filtration. The mother liquor is cooled to yield additional precipitate which is combined with the first precipitate. The total combined crude precipitate after drying under vacuum weighs 28.2 g. The crude precipitate is recrystallized from a solution of ethyl acetate/dimethyl formamide/heptane to yield a first crop of the product; 21.9 g, m.p.=185°–186°. A second crop of discolored product is obtained from the mother liquor, 6.0 g. Then, the product is chlorosulfonated and treated with ammonia to introduce the requisite 3'-sulfamyl group.

What is claimed is:

1. A compound of the formula:

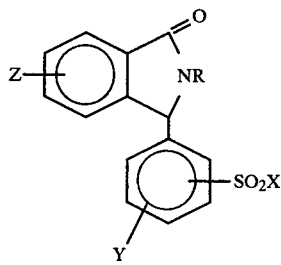

wherein

Z is H, $C_1$–$C_{10}$ alkyl, halo, $C_1$–$C_{10}$ alkoxy, trifluoromethyl, hydroxy, $C_1$–$C_{10}$ alkanoyloxy, or $C_1$–$C_{10}$ alkanoylamino;

Y is H, $C_1$–$C_{10}$ alkyl, halo, $C_1$–$C_{10}$ alkoxy, trifluoromethyl, hydroxy, $C_1$–$C_{10}$ alkanoyloxy, or $C_1$–$C_{10}$ alkanoylamino;

X is F, Cl, Br or $NR_1R_2$ in which $R_1$ and $R_2$ are independently H, $C_1$–$C_{10}$ alkyl, $C_2$–$C_{10}$ alkenyl, $C_2$–$C_{10}$ alkynyl, $C_3$–$C_{10}$ cycloalkyl, $C_6$–$C_{10}$ aryl or $C_7$–$C_{10}$ aralkyl; and R is H, $C_1$–$C_{10}$ alkyl, $C_3$–$C_{10}$ cycloalkyl or $C_7$–$C_{10}$ aralkyl.

2. A compound of the formula:

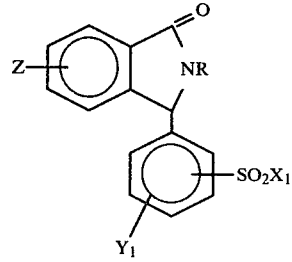

wherein

Z is H, $C_1$–$C_{10}$ alkyl, halo, $C_1$–$C_{10}$ alkoxy, trifluoromethyl, hydroxy, $C_1$–$C_{10}$ alkanoyloxy, or $C_1$–$C_{10}$ alkanoylamino;

$Y_1$ is halo or $CF_3$;

$X_1$ is $NR_1R_2$ wherein $R_1$ and $R_2$ are independently H, $C_1$–$C_{10}$ alkyl, $C_3$–$C_{10}$ alkynyl, $C_2$–$C_{10}$ alkenyl, $C_3$–$C_{10}$ cycloalkyl, $C_6$–$C_{10}$ aryl or $C_7$–$C_{10}$ aralkyl;

R is H, $C_1$–$C_{10}$ alkyl, $C_3$–$C_{10}$ cycloalkyl or $C_7$–$C_{10}$ aralkyl; and salts thereof.

3. The compound according to claim 2 wherein $Y_1$ is 4-halo and $SO_2X_1$ is 3-sulfamyl.

4. 3-(3'-Sulfamyl-4'-chlorophenyl)phthalimidine.

5. The compound according to claim 1 wherein Y is 4-halo and $SO_2X$ is 3-chlorosulfonyl.

6. 3-(3'-Chlorosulfonyl-4'-chlorophenyl)phthalimidine.

* * * * *